United States Patent [19]

Beckman et al.

[11] Patent Number: 5,641,887
[45] Date of Patent: Jun. 24, 1997

[54] EXTRACTION OF METALS IN CARBON DIOXIDE AND CHELATING AGENTS THEREFOR

[75] Inventors: Eric J. Beckman, Edgewood; Alan J. Russell, Wexford, both of Pa.

[73] Assignee: University of Pittsburgh, Pittsburgh, Pa.

[21] Appl. No.: 223,105

[22] Filed: Apr. 1, 1994

[51] Int. Cl.$^6$ .................................................. C07D 401/06
[52] U.S. Cl. ........................ 546/26.2; 546/255; 546/335; 546/336; 526/247; 210/634
[58] Field of Search ........................ 546/255, 262, 546/335, 336; 526/247; 210/634

[56] References Cited

U.S. PATENT DOCUMENTS 4,031,038  6/1977  Grinstead ........................ 525/332.2

OTHER PUBLICATIONS

Hoefling et al "Design and Sythesis of Highly $CO_2$ Soluble Surfactants and Chelating Agents" Fluid Phase Equil. 83 203–212 (1993).

Lainty et al "Separation of et al in as" Analytical Chem. 64 311–315 (1992).

Hseu et al "Spectrophotometric studies of Ni (II) of picolylauion" CA 84: 1273398 (1976).

Hseu et al "Spectrophotometric studies of Co (II) and Cu (III) Chelates of 2–picolyamion" CA 82: 116896u (1975).

Takateru et al "Lubricating agent of megnetic recording medium" CA 113:203657 (1990).

*Primary Examiner*—Ceila Chang
*Attorney, Agent, or Firm*—Reed Smith Shaw & McClay

[57] ABSTRACT

The present invention provides a chelating agent suitable for chelating metals metals in liquid or supercritical carbon dioxide. The chelating agent comprises generally a conventional chelating group and a $CO_2$-soluble functional group covalently attached to the chelating group. Examples of suitable $CO_2$-soluble functional groups include fluorinated polyether groups, silicone groups, fluorinated polyalkyl groups, phosphazene groups and fluorinated polyacrylate groups. The present invention also provides a method of extracting a metal from a matrix containing at least one other material and the metal using such $CO_2$-soluble chelating agents.

8 Claims, 14 Drawing Sheets

| Metal | Preferred CO$_2$ - philic Groups | Chelating Head Group |
|---|---|---|
| Pb | Flouroether<br>Silicone<br>Flouroalkyl |  |
| Hg | Flouroether<br>Flouroalkyl |  |
| As | Flouroether<br>Flouroalkyl |  |
| U | Flouroether<br>Flouroalkyl |  |
| Au | Flouroether<br>Flouroalkyl |  |
| Ni | Flouroether<br>Flouroalkyl |  |
| Cu | Flouroether<br>Flouroalkyl |  |

FE = Fluoroether such as Hexaflouropylene oxide i)

ii)

iii)

iv)

Hydroxyethyl imino diacetic acid

EXTRACTION OF METALS IN CARBON DIOXIDE AND CHELATING AGENTS THEREFOR

FIELD OF THE INVENTION

The present invention relates to a method of extraction of metals in carbon dioxide and also to chelating agents therefor, and especially to the extraction of metals in liquid or supercritical carbon dioxide using novel molecules comprising chelating agents derivatized with functional groups exhibiting suitable $CO_2$ solubility.

BACKGROUND OF THE INVENTION

As a result of their favorable properties, including variable solvent power and low viscosity, supercritical fluids have been employed in a variety of selective extraction processes. Whereas a number of common gases exhibit desirably low critical temperatures (below 100° C.), however, carbon dioxide is without question the most widely-used solvent in supercritical fluid science and technology. McHugh, M. A. and Krukonis, V. J., *Supercritical Fluid Extraction*, Butterworths, Stoneham, Mass. (1986). $CO_2$ is readily available, inexpensive, relatively non-toxic, non-flammable, and exhibits a critical temperature of only 31° C. Carbon dioxide is also one of the few organic solvents which occurs naturally in large quantities. Moreover, because $CO_2$ is a gas under ambient conditions, reduction of liquid or supercritical $CO_2$-based solutions to atmospheric pressure induces essentially complete precipitation of solute, thereby facilitating solute/solvent separation.

Consequently, supercritical $CO_2$ has been tapped as an environmentally-sound, organic solvent in such diverse areas as chromatography, biotechnology, polymerization and extraction of thermally-labile constituents from natural products. McLaren, L., et al., *Science*, 159, 197 (1986); Giddings, J. C., et al., *Science*, 162, 67 (1986); Randolph, T. W. et al., *Science*, 238, 387 (1988); Russell, A. J. and Beckman, E. J., *Appl. Biochem Biotech.*, 31, 197 (1991); Desimone, J. M., et al., *Science*, 257, 5072 (1992); Hubert, P. and Vitzhum, O. G., *Angew. Chem. Int. Ed.*, 17, 710 (1978).

Notwithstanding carbon dioxide's inherent advantages, however, carbon dioxide is a relatively non-polar material and thus will not solubilize highly polar, hydrophilic, or metallic solutes to a significant degree. The most commonly applied strategy for overcoming the poor solubility of polar solutes in $CO_2$ is addition of a co-solvent (also known as a modifier or entrainer), such as a low molecular weight alcohol. Kim, S. and Johnston, K. P., *AIChE J.*, 33, 1603 (1987). The primary disadvantage of this strategy, however, lies in the need to include a large fraction of alcohol to solvate small amounts of solute. Inclusion of large fractions of co-solvents such as alcohol increases the critical temperature of the solvent (now a $CO_2$-alcohol mixture), and thereby increases the required process temperature and pressure. Moreover, even addition of alcohol co-solvents will not solubilize significant quantities (mole fractions greater than $10^{-3}$) of hydrophilic solutes such as metals or proteins.

In the late 1980's, researchers at the University of Texas and Battelle's Pacific Northwest Laboratories investigated the use of commercial surfactants and chelating agents to improve the solubility of polar solutes in non-polar supercritical fluids ("SCF's"). Lemert, R. M.; et al., *J. Phys. Chem.*, 94, 6021 (1990); Fulton, J. L. and Smith, R. D., *J. Phys. Chem.*, 92, 2903 (1988). In that regard, studies show that formation of reverse micelles in supercritical alkanes dramatically increases the SCF solubility of amino acids, water-soluble polymers, proteins, and metal-containing compounds. Beckman, E. J., et al. *Supercritical Fluid Technology*, Bruno, T. J. and Ely, J. F., Eds., CRC Press, Chapter 12 (1991); Johnston, K. P., et al., *Supercritical Fluid Science and Technology*, Johnston, K. P. and Penninger, J. M. L., Eds., ACS Symp. Ser. No. 406 (1989).

However, extension of the use of surfactants/chelating agents to environmentally-benign $CO_2$ has been blocked by the experimental observation that commercially available ionic amphophiles, while highly soluble in alkanes such as ethane and propane, exhibit poor to negligible solubility in carbon dioxide at moderate pressures (i.e., 10–500 bar). This observation holds regardless of whether the agent is a sulfonate, sulfate, ammonium halide, or phosphate. Consani, K. A. and Smith, R. D., *J. Supercrit. Fl.*, 3, 51 (1990). Conventional chelating agents have shown identical trends. Tingey, J. M. et al., *J. Phys. Chem.*, 93, 2140 (1989).

In an attempt to overcome this problem, one study evaluated improvements of the solubility of diethyl thiocarbamate-metal chelates upon replacement of the alkyl groups thereof with fluoroalkyl moieties. Laintz, K. E., et al., *J. Supercrit. Fl*, 4, 194 (1991). Although this strategy led to a two to three order of magnitude increase in solubility (at 50° C., 1500 psi), the greatest absolute solubility (approximately $4.6 \times 10^{-4}$ gm/gm $CO_2$) achieved is too low to act as the basis for a large-scale extraction process.

Another study with fluoroalkyl-functional, twin-tailed sulfonates has shown that a fluoroalkyl chain length of $C_5$ or $C_6$ and greater is required to generate 1–5 weight percent solubility of sulfonates in $CO_2$. Hoefling, T. A., et al., *J. Phys. Chem.* (1991).

At present, the poor solubility of conventional chelating agents in $CO_2$ has prevented process extraction of metals using such chelating agents in $CO_2$. Because of the advantageous properties of $CO_2$ described above, however, it is very desirable to develop a method and chelating agents suitable for performing such extractions.

SUMMARY OF THE INVENTION

Accordingly, the present invention provides a chelating agent suitable for chelating a metal in liquid or supercritical carbon dioxide. The chelating agent comprises a chelating group suitable to chelate the metal and a $CO_2$-soluble functional group covalently attached to the chelating group. The functional group is selected to achieve a chelating agent solubility of at least approximately $10^{-3}$ gram/gram $CO_2$. Preferably, the functional group is selected to achieve a chelating agent solubility of approximately $10^{-2}$ gram/gram $CO_2$. The chelating group preferably comprises an polyiminocarboxylic group (such as an iminodiacetic group, a thiocarbamate group, a dithiol group, a picolyl amine group, a bis(picolyl amine) group or a phosphate group.

To achieve the desired solubility, the $CO_2$-soluble functional group preferably comprises a fluorinated polyether group, a silicone group, a fluorinated polyalkyl group, a phosphazene group or a fluorinated polyacrylate group. More preferably the $CO_2$-soluble functional group comprises a fluorinated polyether group, a silicone group or a fluorinated polyalkyl group. Most preferably, the $CO_2$-soluble functional group comprises a fluorinated polyether group, such as poly(hexafluoropropylene oxide) group.

The present invention also provides a method of extracting a metal from a matrix containing the metal and at least one other material, comprising the steps of: (a) dissolving in a vessel a chelating agent suitable for forming a coordinated complex with the metal in carbon dioxide, the chelating agent comprising a chelating group as described above; and (b) contacting the dissolved chelating agent with the matrix in the vessel. As set forth above, a solubility of at least approximately $10^{-2}$ gram/gram $CO_2$ is preferably achieved.

After contacting the dissolved chelating agent with the matrix for a predetermined period of time, the pressure in the vessel is reduced to precipitate the chelating agent and the coordinated metal. Preferably, the pressure is reduced to atmospheric pressure.

The $CO_2$-soluble chelating agents of the present invention are prepared using a design strategy whereby conventional polar/ionic chelating moieties are derivatized with relatively highly $CO_2$-soluble ("$CO_2$-philic") functional groups. The solubilities of the target molecules in carbon dioxide are several (e.g., three to four) orders of magnitude greater than conventional amphophiles at moderate temperatures and moderate pressures.

The temperature at which the preferred solubility of $10^{-2}$ gm/gm $CO_2$ is achieved is preferably in the range of approximately 0 to 100° C. More preferably the temperature is in the range of approximately 20° to 50° C. Preferably, the pressure at which such solubility is achieved is in the range of approximately 500 to 5000 psi. More preferably, the pressure is in the range of approximately 900 to 3000.

The present compounds extend the application of environmentally-benign, yet nonpolar, $CO_2$ to separation processes previously inaccessible, such as heavy metal extraction from contaminated soil or water. Indeed, extension of the present $CO_2$-philic derivatization scheme to extremely hydrophilic materials such as iminodiacetic acid and thiocarbamate-functional chelates fully demonstrates the usefulness of $CO_2$-philic groups in chelate design.

Moreover, the present invention provides several unique advantages in the extraction of metals from complex matrices such as soil. First, the use of carbon dioxide allows ready extraction (in part, because of the low viscosity of either liquid or supercritical carbon dioxide) followed by ready concentration by depressurization. The ease of concentration allows both recycle of the chelating agent and the carbon dioxide solvent. Second, generation of chelating agents which incorporate $CO_2$-philic functional groups improves the solubility of chelating agents in carbon dioxide by several (three to four) orders of magnitude, thus bringing chelation in supercritical carbon dioxide from the analytical realm to the process realm. Third, use of both silicone and fluoroether $CO_2$-philic groups provides flexibility in the design of target molecules in that such molecule systems can be optimized in terms of required process pressure versus cost of the target molecule system.

DETAILED DESCRIPTION OF THE INVENTION

Figure 1A:
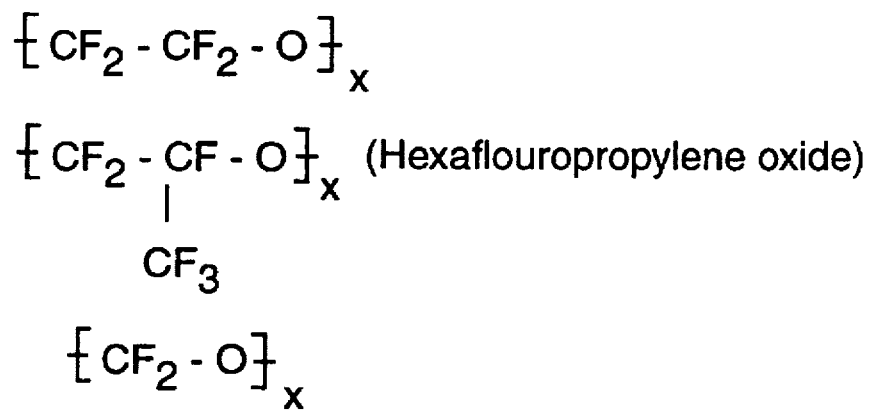
FIG. 1(a) illustrates a general structure of a number of fluoroether functional groups suitable for functionalizing chelating head groups.
Figure 1B:
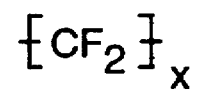
FIG. 1(b) illustrates a general structure of a fluoroalkyl functional group suitable for functionalizing chelating head groups.

Commercially-available chelating agents exhibit poor solubility in $CO_2$. It has been discovered, however, that such chelating agents can be "redesigned" for use in $CO_2$. Consequently, to extend the use of $CO_2$ in separation processes to hydrophilic/metallic solutes, novel $CO_2$-soluble chelating agents have been designed and synthesized.

Identification of Chelating Functional Groups

A chelate is a coordination compound in which an ion of metallic elements such as, for example, U, Pb, Hg, As, Au, Ni, Co and Cu is attached by coordinate links to generally two or more nonmetal atoms in the same molecule. In general, the coordinating atoms are electron donating atoms of the elements O, S, and N. Thus, numerous compounds comprising atoms of O, S and/or N act as chelating agents. See e.g., *Analyst*, 116 (1991) and Calmon, C. and Gold, H., *Ion Exchange for Pollution Control*, Water Pollution Control Technology Series, the disclosures of which are incorporated herein by reference. Although the types of compounds capable of forming coordinate complexes with metal ions are too numerous to categorize beyond the generalization that such compounds comprise O, S, and/or N, examples include compounds comprising thio groups, thiol groups, amine groups, hydroxyl groups, carboxilic groups and/or carbamate groups. Specific examples of chelating agent groups suitable for attachment to the present $CO_2$-philic functional groups include polyaminocarboxilic acid groups (e.g., an iminodiacetic group), thiocarbamate groups, dithiol groups, picolyl amine groups, bis(picolyl amine) groups, and phosphate groups.

Identification of $CO_2$-philic Functional Groups

Like their conventional analogs, the present molecules possess polar head groups designed to accomplish chelation. Unlike conventional compounds of this nature, in which an alkane tail (or tails) is covalently bonded to the head group, however, the present target molecules possess a hydrophobic tail comprising a functional group designed to interact favorably, in a thermodynamic sense, with carbon dioxide. Such functional groups may be referred to as "$CO_2$-philic" groups.

Whereas numerous reports suggest that the solvent power of carbon dioxide is similar to that of hexane, it has now been discovered that these suggestions are incorrect. Design of $CO_2$-philic functional groups must incorporate knowledge of the molecular properties of carbon dioxide. In fact, it has been discovered that many of the most $CO_2$-philic functional groups available are almost entirely insoluble in alkanes.

Although the solubility parameter (a measure of bulk solvent properties) of supercritical carbon dioxide approaches that of hexane above 300 bar at 40° C., specific interactions involving $CO_2$ and those involving hexane will differ greatly at the molecular level. Unlike hexane, $CO_2$ is a Lewis acid and possesses a quadrupole moment. Indeed, studies of molecular level solvent properties of $CO_2$ have been more closely likened to the behavior of ethyl acetate, or perhaps even acetone, rather than hexane. Walsh, J. M. et al., *Fluid Phase Equil.*, 33, 295 (1987); Nyatt, J. A., *J. Org. Chem*, 49, 5097 (1984).

Even the above generalizations, however, must be approached with caution. Reliance on a "$CO_2$ substitute" in screening studies to identify $CO_2$-philic compounds or functional groups will invariably lead to misidentification of such compounds.

Whereas fluoroether and silicone polymers exhibit high solubilities in $CO_2$ at moderate pressures, polyolefin waxes of comparable molecular weight exhibit solubilities which are several orders of magnitude lower at the pressures examined. These results would not be expected if the solvent power of $CO_2$ were simply "like that of hexane". Furthermore, fluoroethers are generally immiscible with pentane or hexane, compounds which have been promoted as potential screening agents for $CO_2$-solubility.

Given the known physical properties of $CO_2$, and extensive literature data on supercritical $CO_2$/solute phase behavior (see e.g., Dandge, D. K et al., *IEC Prod. Res. Dev.*, 24, 162 (1985); Francis, A. W., *J. Phys. Chem.*, 58, 1099 (1954); U.S. Pat. No. 4,913,235; and Iezzi, A., *Fluid Phase Equil*, 52, 307 (1989)), it has been determined that inclusion of the particular functional groups of Table 1 in a solute molecule will contribute to relatively high solubility in $CO_2$.

TABLE 1

| Functional Groups Which Interact Favorably With Carbon Dioxide | |
|---|---|
| Functional Groups | Properties Leading to Favorable Interaction |
| Fluorinated Polyethers (e.g., Hexafluoropropylene Oxide) | Low solubility parameter (4–6 $(cal/cm^3)^{0.5}$), electron-donating capability |

TABLE 1-continued

| Functional Groups Which Interact Favorably With Carbon Dioxide | |
|---|---|
| Functional Groups | Properties Leading to Favorable Interaction |
| Silicones (e.g., Dimethyl Siloxane) | Low solubility parameter (7–9 $(cal/cm^3)^{0.5}$) |
| Fluoroalkyls | Low solubility parameter (6–7 $(cal/cm^3)^{0.5}$), low dipolarity polarizability parameter, (−0.5–0.0) |
| Fluorinated polyacrylates | Low solubility parameter, electron-donating capability |
| Poly(phosphazenes) | Electron-donating capability |

Figure 1C:
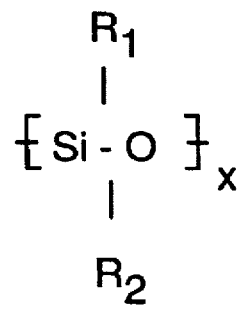
FIG. 1(c) illustrates a general structure of a silicone functional group suitable for functionalizing chelating head groups.
Figure 1D:
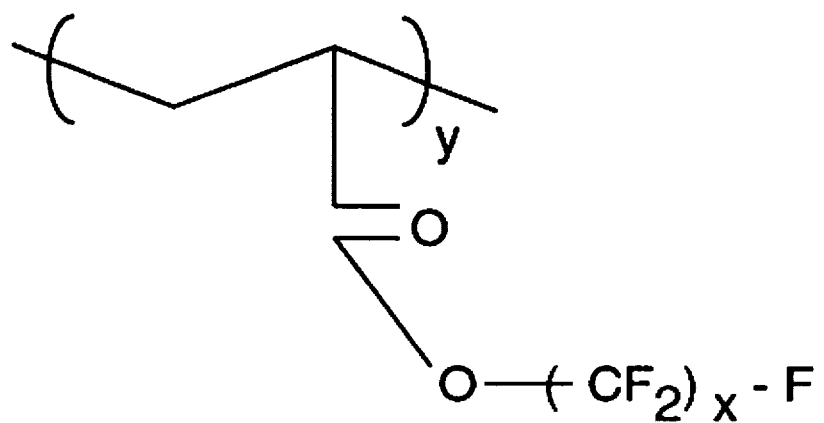
FIG. 1(d) illustrates a general structure of a fluorinated polyacrylate functional group suitable for functionalizing chelating head groups.
Figure 1E:
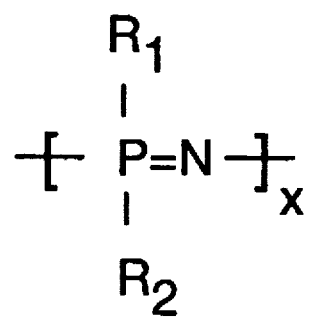
FIG. 1(e) illustrates a general structure of a phosphazene functional group suitable for functionalizing chelating head groups.

The $CO_2$-philic groups of Table 1 are illustrated schematically in FIG. 1(a)–1(e). In FIGS. 1(c) and 1(e), $R_1$ and $R_2$ can, in general, be any alkyl, aromatic or alkyl-aromatic group. Preferably $R_1$ and/or $R_2$ comprise a fluorinated alkyl group.

Previous studies with fluoroalkyl sulfonate surfactants show that solubility in carbon dioxide rises significantly upon replacement of —$CH_2$— with —$CF_2$— in such compounds. Hoefling, T. A., et al., *J. Phys. Chem.*, supra, the disclosure of which is incorporated herein by reference. These Studies (performed with fluoroalkyl-functional, twin-tailed sulfonates) showed that a fluoroalkyl chain length of $C_5$ or $C_6$ and greater is required to generate 1–5 weight % solubility of sulfonates in $CO_2$. It is believed that fluoroalkyls will exhibit similar $CO_2$-philic behavior in solubilizing metal chelating groups in $CO_2$.

Another study recently showed that fluorinated polyacrylates are extremely soluble in carbon dioxide. Desimone, J. M., et al., *Science*, 257, 5072 (1992), the disclosure of which is incorporated herein by reference. This study demonstrated orders-of-magnitude improvement in $CO_2$-solubility of high molecular weight polymers of fluoroacrylates compared to their alkyl analogs. It is, therefore, believed that fluorinated polyacrylates will also be suitable for use in the present invention.

Previously, solubilities of chelating agents greater than approximately $4.6 \times 10^{-4}$ have been unattainable. Under the present invention, however, solubilities greater than $10^{-3}$ are readily attainable. To enable viable process extraction, however, a solubility of at least $10^{-2}$ gm chelating agent/gm $CO_2$ is preferably attained. In this regard, fluoroether and silicone derivatization has been found to increase the solubility of conventional chelating agents by three to four orders of magnitude, resulting in absolute solubilities in the range of approximately $10^{-2}$ to $10^{-1}$ gm/gm $CO_2$ (i.e., 1 to 10 wt %).

Of the functional groups of Table 1, fluoroether compounds exhibit the highest $CO_2$-solubility. Thus, fluoroether-derivatized chelating agents generally exhibit higher solubilities than chelating agents derivatized with other functional groups previously studied at a given temperature and pressure. Tables 2 and 3 provide solubility data for a fluoroether-functionalized dithiol chelating agent and a fluoroether-functionalized picolyl amine chelating agent, respectively. As seen, solubilities in the range of approximately 2.10 to 4.40 wt % were attained.

TABLE 2

| Fluorether derivatized dithiol | | |
|---|---|---|
| $CO_2$ | wt % | Cloud Point |
| 19.5 | 4.41 | 940 |
| 23.2 | 3.71 | 970 |
| 27.5 | 3.13 | 980 |
| 31.9 | 2.70 | 1000 |
| 36.1 | 2.38 | 1020 |
| 40.4 | 2.13 | 1040 |

TABLE 3

| Fluorether derivatized picolyl amine | | |
|---|---|---|
| $CO_2$ | wt % | Cloud Point |
| 25.3 | 4.34 | 1000 |
| 29.3 | 3.75 | 1023 |
| 33.3 | 3.30 | 1080 |
| 37.3 | 2.94 | 1025 |

In general, the solubility of derivatized chelating agents can be increased by raising the pressure. However, the pressure is preferably in the range of approximately 500 to 5000 psi and, more preferably, in the range of approximately 900 to 3000 psi. The temperature is preferably in the range of approximately 0 to 100° C. and, more preferably, in the range of approximately 20 to 50° C.

To ensure adequate solubility is achieved, at least three repeat units of a fluoroether such as hexafluoropropylene oxide (resulting in a molecular weight of approximately 500) are attached to a chelating group. In the case of a silicone functional group, at least six repeat units are preferably attached (resulting in a molecular weight of approximately 500). In the case of a fluoroalkyl functional group, at least six repeat units are preferably attached, resulting in a molecular weight of 300). In the case of a fluorinated polyacrylate functional group, at least three repeat groups are preferably attached (resulting in a molecular weight of approximately 1200). In the case of a phosphazene functional group, at least six repeat units are preferably attached.

Figure 1F:
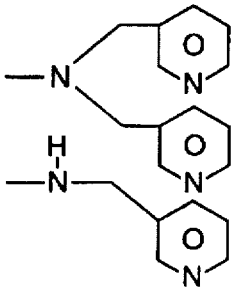
FIG. 1(f) illustrates a number of preferred structures for chelating agents designed to extract certain metals.
Figure 1F:
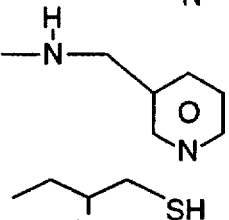
Figure 1F:
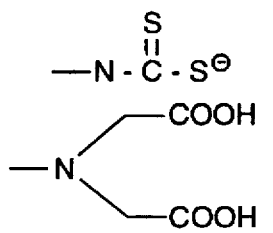
Figure 1F:
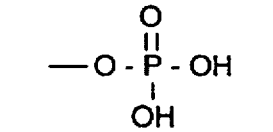
Figure 1F:
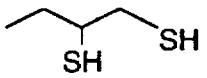
Figure 1F:
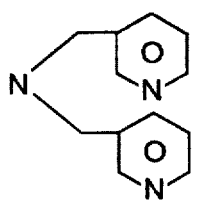
Figure 1F:
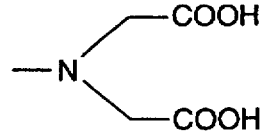

Several chelating head groups for use the present invention were chosen as a result of previous studies showing their efficacy in coordinating one or more metals. In that regard, FIG. 1(f) illustrates a number of such chelating head groups, corresponding preferred $CO_2$-philic functional groups and the metal the resultant target molecules are designed to extract.

In general, non-ionic chelating head groups have been found to work well with all the $CO_2$-philic functional groups of Table 1 studied. Preferably, ionic chelating head groups (which are particularly insoluble in $CO_2$) are functionalized with strongly $CO_2$-philic functional groups such as fluoroethers to achieve suitable solubility at moderate temperatures and pressure fluoroethers.

Figure 1G:
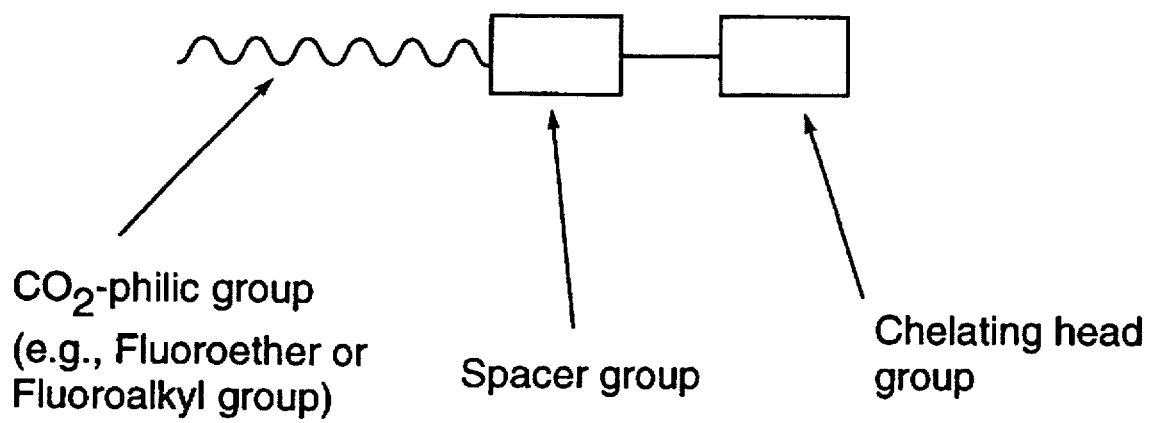
FIG. 1(g) illustrates schematically the structure of a chelating agent incorporating a spacer group for minimizing adverse effects of a strong electron withdrawing $CO_2$-philic group upon the chelating head group.

Further, fluoroethers and fluoroalkyls are strong electron withdrawing agents, a property adversely affecting chelation. Therefore, in some cases when fluoroethers and fluoroalkyls are used as a $CO_2$-philic functional group, a non-electron withdrawing spacer group is preferably inserted between the fluoroether or the fluoroalkyl and the chelating head group (see FIG. 1(g)) to minimize the detrimental effect of the electron withdrawing group. Preferably the spacer group is a $(CH_2)_x$ group wherein preferably x>3.

Synthesis of Fluoroalkyl- and Fluoroether-functional Chelating Agents

Figure 2A:
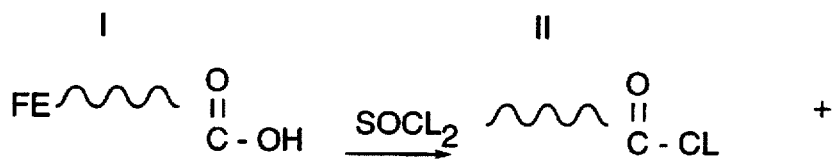
FIG. 2(a) illustrates schematically a synthetic scheme for production of fluoroalkyl- and fluoroether-functionalized chelating agents.
Figure 2A:
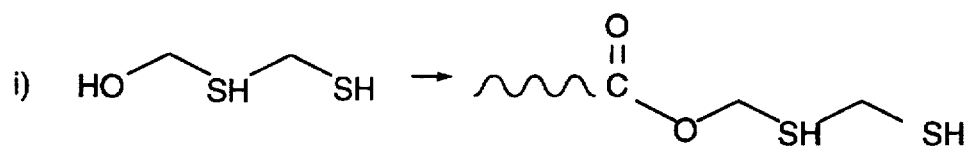
Figure 2A:
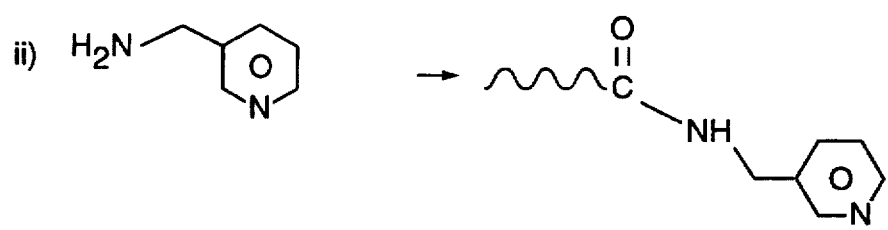
Figure 2A:
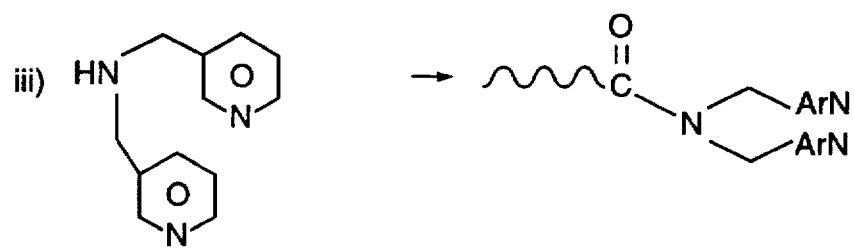
Figure 2A:
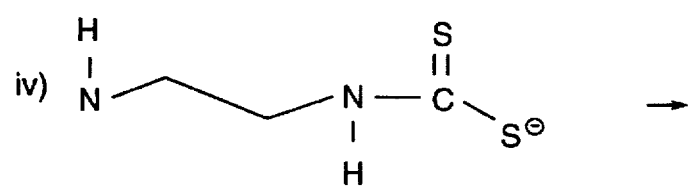
Figure 2A:
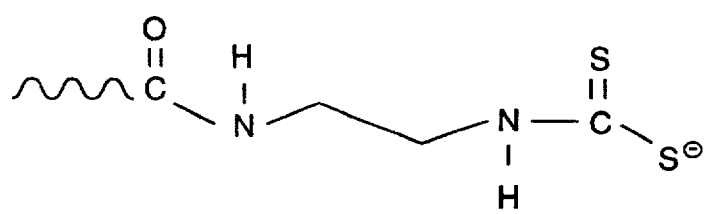

A general synthetic scheme to prepare the fluoroether-functionalized chelating agents of the present invention is illustrated schematically in FIG. 2(a). The synthetic strategy was developed in an attempt to employ chemical routes which are both as convergent as possible and as high yield as possible.

Figure 2B:
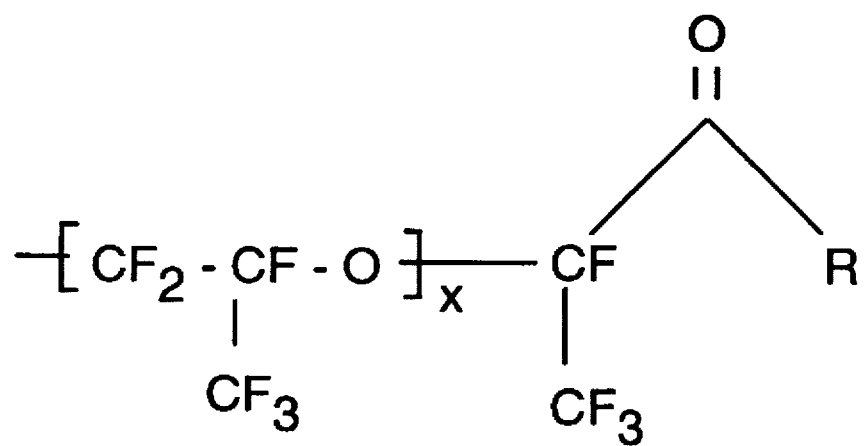
FIG. 2(b) illustrates a general structure of fluoroether-functional chelating agents prepared using a hexafluoropropylene oxide precursor.

Generally, to synthesize the $CO_2$-soluble chelating agents, an acyl chloride meta-precursor(II) was first prepared from the acid-functional fluoroether (I) via reaction with thionyl chloride ($SOCl_2$). The acid chloride was then used to prepare each of the target molecules by reaction with a hydroxy- or amino-functionalized chelating head group (see i-iv of FIG. 2(a)). The general structure for resultant hexafluoropropylene oxide functionalized chelating agents is shown schematically in FIG. 2(b), in which R represents the chelating head group. In the case of a hexafluoropropylene oxide having a molecular weight of approximately 2500, the value of x in FIG. 2(b) is 14.

Fluoralkyl-functionalized chelating agents may be synthesized via a similar scheme to that shown in FIG. 2(a). In general, an acyl chloride precursor may be prepared from an acid-functionalized fluoroalkyl. The acyl chloride is then used to prepare the target molecules as set forth above. One may alternatively obtain commercially available acyl-chloride-functionalized fluoroether and fluoralkyl for use in synthesis of the present chelating agents.

EXAMPLES

Oligomers of hexafluoropropylene oxide, capped (mono) with a carboxylic acid group, were received from DuPont (Krytox functional oils of approximately 2500, 5000, and 7500 molecular weights). In that regard, an approximately 2500 molecular weight, mono-carboxy terminated oligomer of hexafluoropropylene oxide (Krytox 157FSL, DuPont) was transformed to the acyl chloride using thionyl chloride. In a typical experiment, 10 g of Krytox 157FSL was dissolved in 50 ml of a mixture of $C_2Cl_4F_2/C_2Cl_3F_3$ or, preferably, in perfluoromethyl cyclohexane; to which was added thionyl chloride and dimethyl formamide (Aldrich), each in approximately 100% molar excess (e.g. 0.95 gram of thionyl chloride (8 mmole) and 0.58 grams (8 mmole) of dimethyl formamide) in a reaction flask equipped with a dry-ice condenser. The temperature was raised to approximately 80° C., and the mixture stirred for several hours (approximately six hours) under an inert atmosphere. Following removal of excess solvent and residual reactant under vacuum the product was analyzed for acyl chloride (FT-IR, carbonyl peak shifts from 1776 to 1809 $cm^{-1}$, $^1H$ NMR, disappearance of COOH proton at 9.63 ppm, $^{13}C$ NMR, shift of carbonyl carbon peak from 161 to 163 ppm). The acyl chloride was then used to prepare each of the target molecules.

a. Synthesis of picolyl amine, bis(picolyl amine) and dithiol chelates

Chelating agents containing dithiol (i in FIG. 2(a)), picolyl amine (ii in FIG. 2(a)) and bis(picolyl amine) (iii in FIG. 2(a)) functional groups have been prepared. In a typical experiment, 10 grams of fluoroether acyl chloride (I) (4 mmole) were dissolved in 50 $cm^3$ dry $C_2Cl_3F_3$ (freon 113). Subsequently, 0.58 grams picolyl amine (6 mmole, Aldrich) in 10 $cm^3$ dry THF were added, as well as an amount of a crosslinked, aminopyridine-functional resin (PolyDmap, Reilly Industries) to scavenge HCl. After stirring for several hours, the PolyDmap was removed by filtration, the solvent removed under vacuum, and the product was washed several times with ether. Characterization of the product showed the formation of the amide (FT-IR, 1720 $cm^{-1}$).

Chelating agents comprising bis(picolyl amine) and dithiol groups were prepared analogously from bis(picolyl amine) and 2, 3 dithio-1-propanol (Aldrich), respectively.

b. Synthesis of thiocarbamate-functionalize chelating agents.

For a chelating agent comprising thiocarbamate (iv of FIG. 2(a)), the chelating head group was prepared as follows: N,N' dimethyl ethylene diamine was dissolved in dry ether at −70° C., after which butyl lithium (1 molar solution in ether) was added dropwise to a 1:1 molar ratio with the diamine. After approximately one hour, carbon disulfide (1:1 molar ratio to diamine) was added with stirring while raising the temperature slowly to 0° C. The product was recovered from the solvent conventionally, and was then dissolved in DMSO, and added to a solution of acyl chloride precursor (I) in a dioxane/freon 113 mixture, with a crosslinked HCl scavenger resin present. The product was subsequently recovered from the solvent conventionally.

c. Synthesis of purine and thio-functional purine chelates.

Figure 2C:
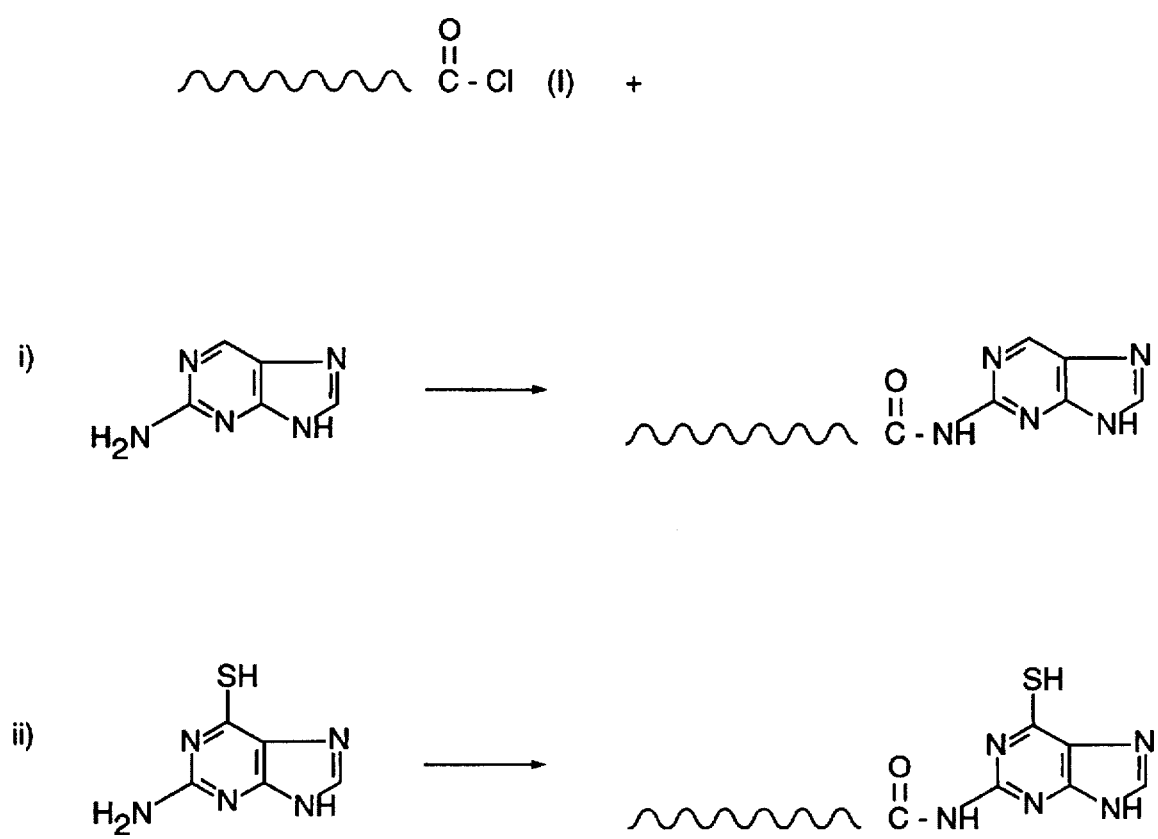
FIG. 2(c) illustrates schematically a synthetic scheme for production of fluoroalkyl- and fluoroether-functionalized chelating agents comprising a purine group or a thio-functional purine group.

In the case of purine (i of FIG. 2(c)) and thio-functional purine (ii of FIG. 2(c)), the chelating head group compounds were dissolved in DMSO, then added to a solution of fluoroether acyl chloride precursor (I) and PolyDmap in a $C_2Cl_3F_3$/Dioxane mixture.

d. Synthesis of phosphate ester chelates.

Figure 2D:
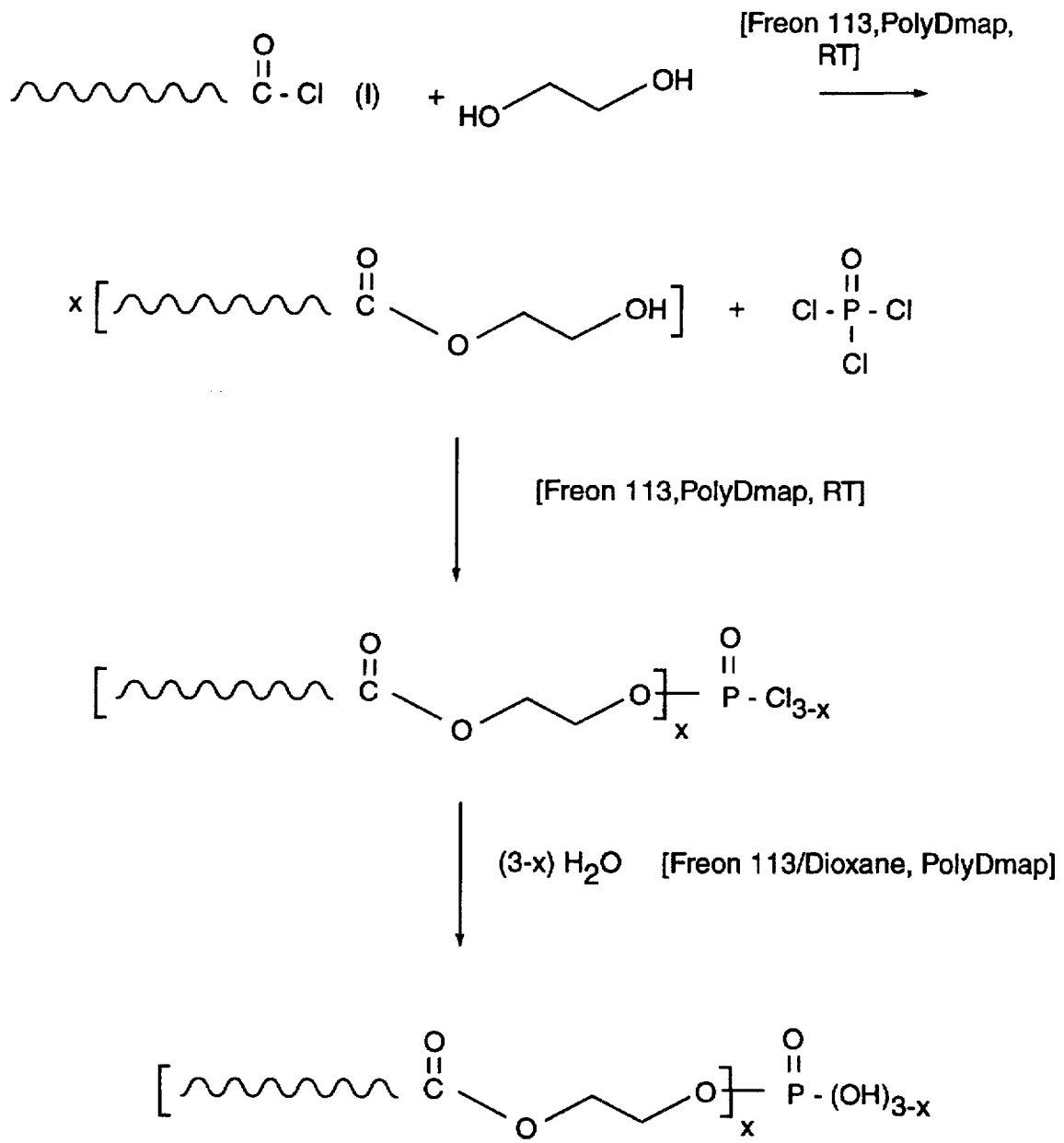
FIG. 2(d) illustrates schematically a synthetic scheme for production of fluoroalkyl- and fluoroether-functionalized chelating agents comprising a phosphate ester group.

A phosphate ester chelating agent (see FIG. 2(d)) was prepared by reaction of acyl chloride (I) with a large molar excess of ethylene glycol (at room temperature (RT), in previously dried freon 113 and in the presence of an HCl scavenger such as PolyDmap) to generate a hydroxy functional product. The hydroxy functional product was reacted with phosphorous oxychloride (in Freon 113, at room temperature and in the presence of an HCl scavenger) in an appropriate ratio to generate single, twin or triple tailed materials as desired. Excess water was added to the product to hydrolize remaining P-Cl bond.

e. Synthesis of aminodiacetic acid chelates.

Figure 2E:
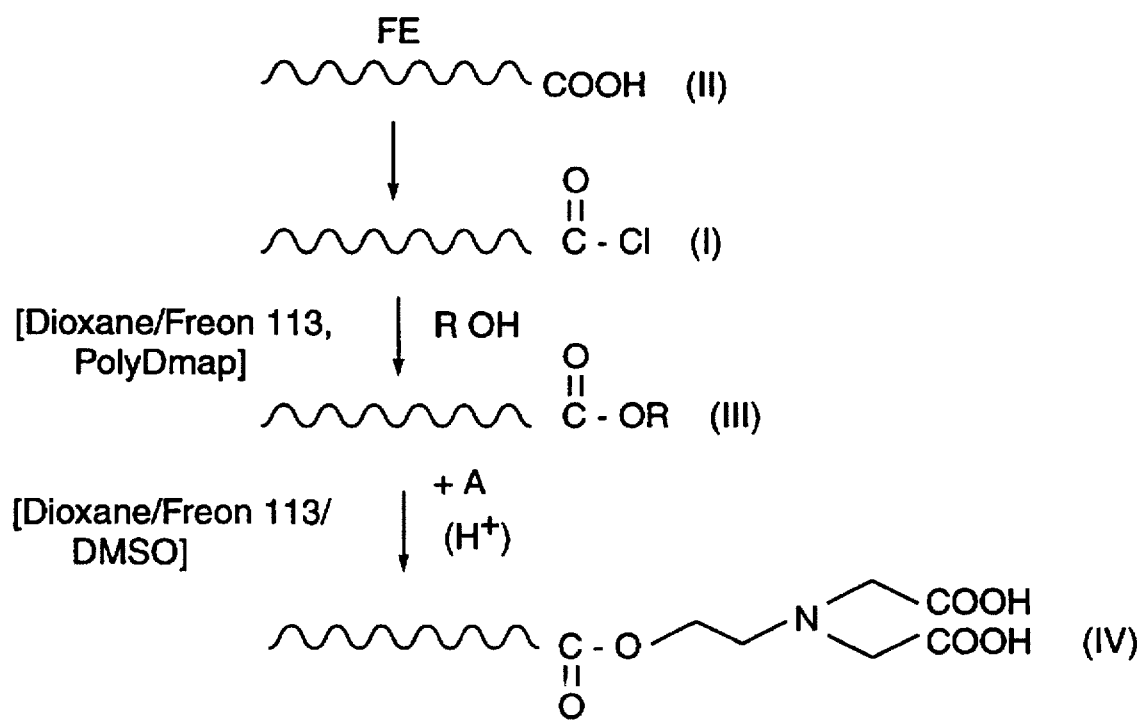
FIG. 2(e) illustrates schematically a synthetic scheme for production of fluoroalkyl- and fluoroether-functionalized chelating agents comprising an iminodiacetic acid group.
Figure 2E:
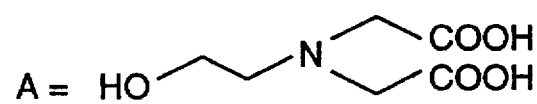

Because iminodiacetic acid is soluble only in water, the reaction scheme is somewhat different than those described above and is set forth schematically in FIG. 2(e). An iminodiacetic acid ("IDA") functional material is prepared by reaction of acyl chloride precursor (I) with, for example, nitrophenol or N-hydroxy succinimide to form an activated ester (III). This reaction takes place at room temperature in an appropriate solvent (such as a Dioxane/Freon 113 mixture) and in the presence of an HCl scavenger such as PolyDmapo Activated ester (III) is reacted with hydroxyethyl imino diacetic acid (A) with a small amount of acid catalyst in an appropriate solvent (such a Dioxane/Freon 113 mixture) at approximately 50° to 70° C. to give product (IV).

Synthesis of silicone-functional chelating agents

Figure 3:
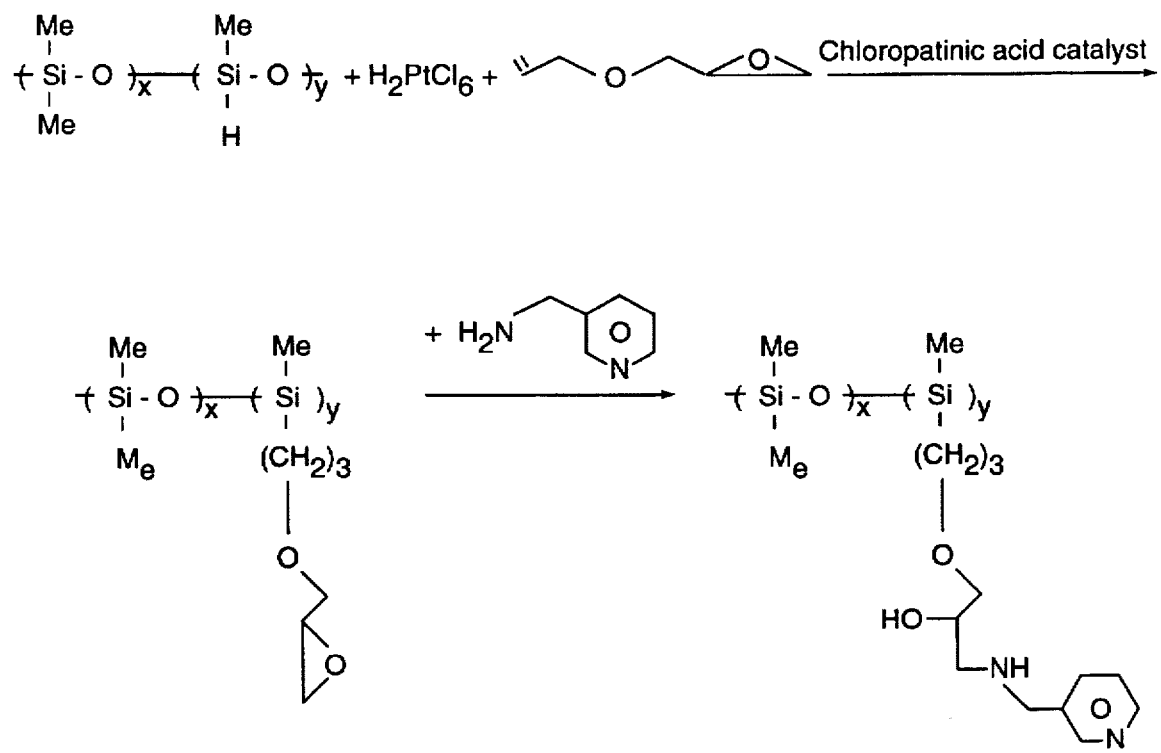
FIG. 3 illustrates schematically a synthetic scheme for production of silicone-functionalized chelating agents.

A synthetic scheme for preparation of silicone-functional chelating agents is shown in FIG. 3. Linear, mono-functional molecules as well as branched multi-functional molecules were evaluated. Branched molecules were synthesized via functionalization of a hydromethyl/dimethyl siloxane copolymer (Huls-Petrarch PS123.5) with allyl glycidal ether (AGE, Aldrich).

Using $^{29}Si$ NMR, the PS123.5 precursor was ascertained to possess the structure $(DMS)_{24}(HMS)_6$ (where DMS refers to dimethyl siloxane and HMS to hydromethyl siloxane), providing six reactive sites per molecule. During the synthesis of the silicone-functionalized chelating agents, each HMS residue was functionalized either with AGE, or with a silicone "blocking agent", allyl tris(trimethylsiloxy) silane (ATSS; Huls-Petrarch)

In a typical experiment, 10 g of PS123.5 is dissolved in 100 $cm^3$ of dry toluene in a 250 $cm^3$ three neck round bottom flask; varying amounts of AGE are then added, depending on the ultimate number of chelating head groups desired (1 to 6). Next, 30 μl of a 0.1M chloroplatinic acid (Aldrich) solution in isopropanol is added, and the mixture refluxed for 6 hr. Next, the appropriate amount of ATSS is added to block the remaining hydromethyl groups, an additional 30 μl of the catalyst is injected, and the mixture is refluxed overnight. Following removal of the solvent, residual AGE, and ATSS under vacuum, the product is characterized using FT-IR (disappearance of the strong Si—H signal at 2150 $cm^{-1}$) and $^1H$ NMR (integrity of the oxirane group).

a. Synthesis of silicone-functional picolyl amine and bis(picolyl amine) chelates.

Following confirmation of production of the AGE-functional silicone, the pendant oxirane groups are reacted with amino- or hydroxyl-functional chelating head groups. For example, the AGE-functional silicone was reacted with a large molar excess of picolyl amine or bis(picolyl amine) in an appropriate solvent (e.g., chloroform) and reflux at 50° to 70° C. for several hours, followed by solvent removal under vacuum.

The procedure for synthesis of the linear silicone-functional chelating agents is analogous to that described above, except that a HMS-DMS-DMS-HMS precursor (Huls-Petrarch 09814) is employed. One end functionalized with AGE, the other with the ATSS blocking agent. The pendant oxirane is then reacted with an amino- or hydroxyl-functional chelating head group as described above.

Characterization

Solubility in Carbon Dioxide

Figure 4:
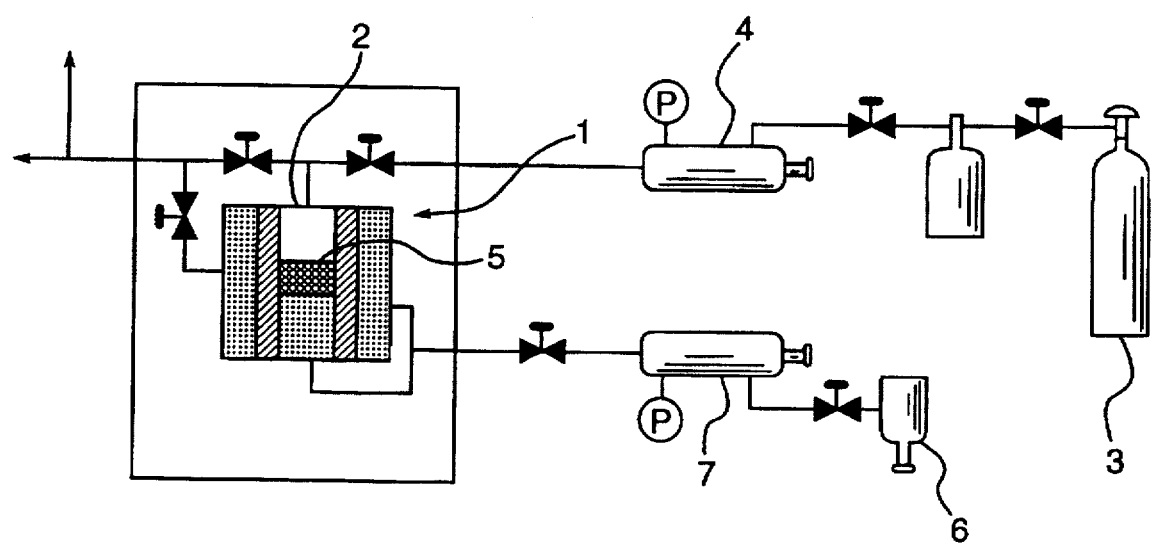
FIG. 4 is a schematic illustration of an apparatus for performing solubility studies.

Phase behavior of the chelating agents in carbon dioxide (Bone dry grade) was performed using a high pressure, variable volume view cell 1 (D. B. Robinson and Assoc.), shown in FIG. 4. Typically, a known amount of chelating agent is added to the top of the quartz tube sample cell 2, as well as a number of steel ball bearings (to provide mixing). The tube is then sealed inside the steel housing, and a known volume of carbon dioxide (from cylinder 3) at its vapor pressure is injected via a compressor using a Ruska syringe pump 4. Quartz sample tube 2 contains a floating piston 5 which separates the sample from the pressure-transmitting fluid, in this case silicone oil from reservoir 6. The pressure on the sample is raised (via movement of the piston due to injection of silicone oil by a second Ruska pump 7) to a point where a single phase is present (mixing is accomplished via motion of the ball bearings (not shown) upon rocking of the entire cell). The pressure is then lowered via slow withdrawal of silicone oil from beneath the piston until the first signs of turbidity appear. This procedure is repeated until the cloud point is known to within a few psi. The pressure is then lowered to the vapor pressure, additional carbon dioxide is injected, and a new cloud point is measured; eventually an entire cloud point curve is mapped.

Figure 5A:
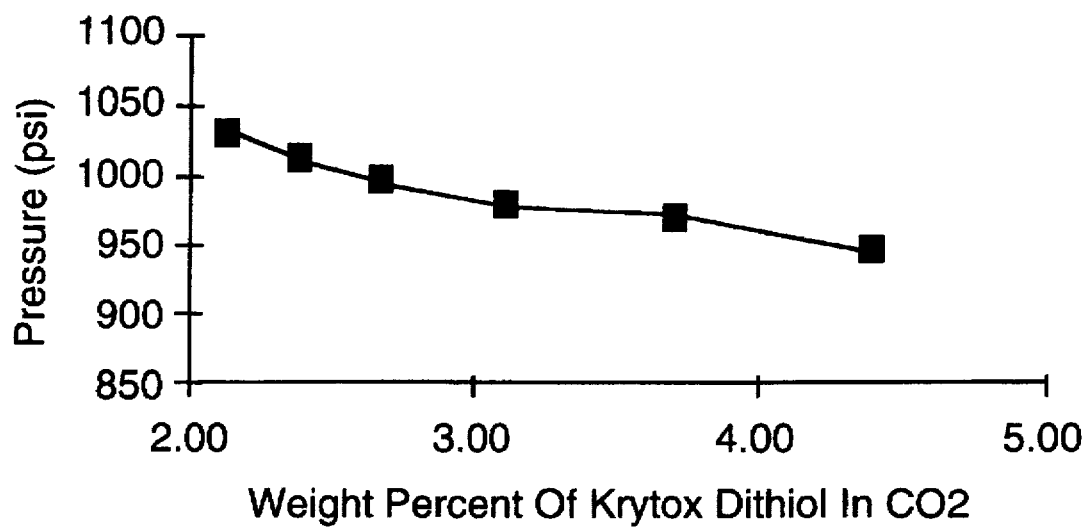
FIGS. 5(a) and (b) illustrate the solubility of two fluoroether-functionalized (2500 molecular weight poly (hexafluoropropylene oxide) chelating agents in $CO_2$ at 40° C.
Figure 5B:
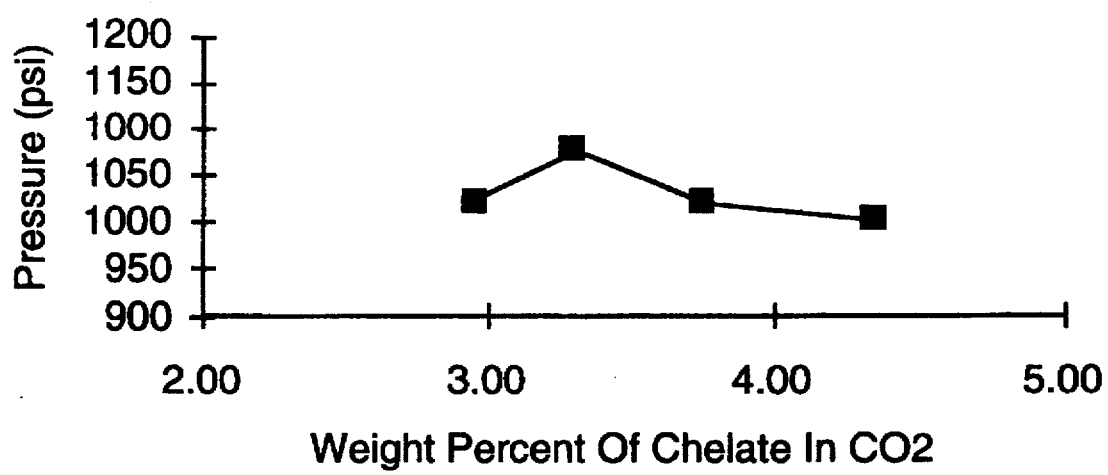
FIG. 5(c) illustrates the solubility of two silicone-functionalized chelating agents at 40° C.
Figure 5C:
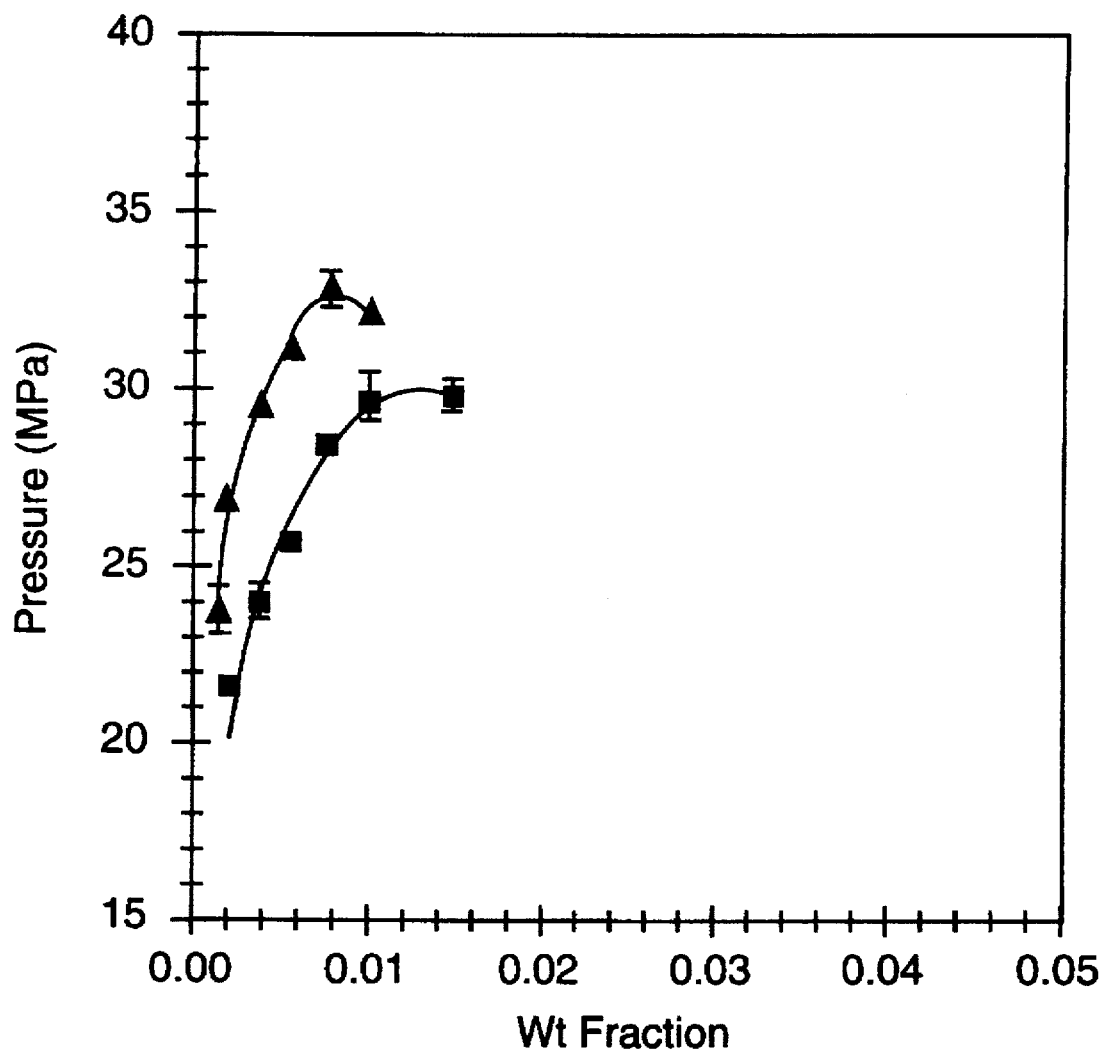

Cloud point curves (FIG. 5(a) and 5(b) for dithiol and picolyl amine, respectively) show that the fluoroether-functional chelating agents are extremely soluble in $CO_2$ at moderate pressures and 40° C. FIG. 5(e) illustrates cloud point curves for a silicone-functionalized picolyl amine (squares) and bis (picoly/amine) (triangles) at 40° C.

Extraction Studies.

In extraction studies, Laboratory sand is spiked with metal according to the following procedure: 50 grams of sand (Fisher) is slurried with 100 $cm^3$ of an aqueous solution of, for example, lead nitrate for several hours. The water is then removed under vacuum while stirring vigorously in the rotary evaporator. Metal loadings of 1 to 3 milliequivalent per 100 grams of sand are thus prepared. A pre-extraction "blank" is then generated by slurrying a sample of the spiked sand with a hot nitric acid solution for several hours, then analyzing the aqueous extractant via atomic absorption spectroscopy (AAS).

Extraction is performed using the chelating agents of the present invention in both freon 113 and $CO_2$ for comparison. In the case of the freon, a solution of chelating agent is slurried with the spiked sand for several hours, after which time the sand is removed by filtration, washed with additional freon, then dried. The sand is then subjected to nitric acid digestion as before, and the aqueous extract analyzed for metal concentration via AAS. In addition, an extraction using pure freon 113 is performed as an additional blank.

In extractions using carbon dioxide, spiked sand plus the chelating agent are added to the extraction vessel (40 cm³, 7500 psi max., constructed at University of Pittsburgh), following which the system is pressurized via an Eldex piston pump. Upon reaching the operating pressure, the Eldex pump is shut off, and carbon dioxide is circulated through the system using the high pressure gear pump (Micropump), while the sand slurry is stirred via a magnetic stir bar (a filter at the vessel outlet prevents entrainment of sand by the $CO_2$). After 30 minutes of recirculation, pure $CO_2$ is pumped through the system by the Eldex pump, exiting at the back pressure regulator (Tescom), where the pressure drops to atmospheric and the solute precipitates and is collected. The system is then depressurized and the sand collected for nitric acid digestion and analysis for residual metal content.

Several experiments, showed that a bis(picolyl amine) functional fluoroether will extract nickel and lead from samples of laboratory sand which had been spiked with a nickel salt and a lead salt, respectively.

Although the invention has been described in detail for the purposes of illustration, it is to be understood that such detail is solely for that purpose and that variations can be made therein by those skilled in the art without departing from the scope of the invention except as it may be limited by the claims.

What is claimed is:

1. A chelating agent suitable for forming coordinated complexes with a metal in liquid and supercritcal carbon dioxide of covalently bonded (i) a bispicolylamino group, (ii) a non-electron withdrawing spacer group selected $(CH_2)_x$ and (iii) a $CO_2$ soluble functional group selected from $(CF_2CF_2O)_x$, $(CF_2O)_x$ and $(CF_2(CF_3)FO)_x$, wherein x is selected to be $\geq 3$ and is selected to minimize the electron withdrawing effect of the $CO_2$ soluble functional group and to achieve a chelating agent solubility of at least a $10^{-3}$ gram/gram $CO_2$.

2. The chelating agent of claim 1 having the structure.

3. The chelating agent of claim 1 wherein a solubility of at least $10^{-2}$ gm/gm $CO_2$ is attained at a temperature in the range of approximately 0 to 100° C.

4. The chelating agent of claim 3 wherein a solubility of at least $10^{-2}$ gm/gm $CO_2$ is attained at a temperature in the range of approximately 20° to 50° C.

5. The chelating agent of claim 1 wherein a solubility of at least $10^{-2}$ gm/gm $CO_2$ is attained at a pressure in the range of approximately 500 to 5000 psi.

6. The chelating agent of claim 1 wherein a solubility of at least $10^{-2}$ gm/gm $CO_2$ is attained at a pressure in the range of approximately 900 to 3000 psi.

7. The chelating agent of claim 1 wherein the fluorinated polyether group is a poly(hexafluoropropylene oxide) group.

8. The chelating agent of claim 1 wherein the spacer group is —$(CH_2)_3$—.

* * * * *

UNITED STATES PATENT AND TRADEMARK OFFICE
CERTIFICATE OF CORRECTION

PATENT NO. : 5,641,887
DATED : June 24, 1997
INVENTOR(S) : Eric J. Beckman and Alan J. Russell It is certified that error appears in the above-indentified patent and that said Letters Patent is hereby corrected as shown below:

Claim 1 Column 12, line 13 after "$(CF_3CF_2O)_x$" insert -- a space --.

Claim 2 Column 12, line 18 after "having the structure" delete "." and insert --

Signed and Sealed this

Nineteenth Day of August, 1997

Attest:

BRUCE LEHMAN

Attesting Officer

Commissioner of Patents and Trademarks